United States Patent [19]

Grollier et al.

[11] 4,220,447
[45] Sep. 2, 1980

[54] SOLID, FROZEN STABILIZED HAIR DYE

[75] Inventors: Jean-Francois Grollier, Paris; Christian Monnais, Neuilly-sur-Seine, both of France

[73] Assignee: L'Oreal, Paris, France

[21] Appl. No.: 605,831

[22] Filed: Aug. 19, 1975

Related U.S. Application Data

[63] Continuation of Ser. No. 275,464, Jul. 27, 1972, abandoned.

[30] Foreign Application Priority Data

Jul. 29, 1971 [LU] Luxembourg ............................ 63634

[51] Int. Cl.$^2$ .............................................. A61K 7/13
[52] U.S. Cl. ............................................. 8/406; 8/32
[58] Field of Search ................. 8/10, 10.2, 10.1, 11, 8/32

[56] References Cited

U.S. PATENT DOCUMENTS

| | | | |
|---|---|---|---|
| 3,413,073 | 11/1968 | Bugaut et al. | 8/10.2 X |
| 3,506,389 | 4/1970 | Charle et al. | 8/10.2 |
| 3,516,778 | 6/1970 | Brunner | 8/10.2 |
| 3,674,902 | 7/1972 | Kalopissis et al. | 8/10.2 X |
| 3,679,102 | 7/1972 | Charle et al. | 8/10.2 X |
| 3,698,852 | 10/1972 | Pantzer et al. | 8/10.2 |
| 3,712,790 | 1/1973 | Kalopissis et al. | 8/10.2 |
| 3,730,677 | 5/1973 | Kalopissis et al. | 8/10.2 |
| 3,792,090 | 2/1974 | Kalopissis et al. | 8/10.2 X |
| 3,861,868 | 1/1975 | Milbrada | 8/10.2 |

*Primary Examiner*—Natalie Trousof
*Assistant Examiner*—Vera C. Clarke
*Attorney, Agent, or Firm*—Cushman, Darby & Cushman

[57] ABSTRACT

A cosmetic composition which at ambient temperature comprises a solution in a water or hydroalcoholic solvent of at least one cosmetic component which in said solution at ambient temperature is not stable, can be preserved, stabilized and packaged by freezing said composition and storing it at a temperature below its freezing point.

1 Claim, No Drawings

SOLID, FROZEN STABILIZED HAIR DYE

This is a continuation of application Ser. No. 275,464 filed July 27, 1972, now abandoned.

The present invention relates to a process for preserving and packaging cosmetic compositions, such as hair dye compositions, hair bleaching compositions, hair restructuring compositions and compositions for reducing oily and greasy appearance of the hair and scalp as well as compositions for the care of skin. More particularly, the present invention relates to a cosmetic composition for the hair and skin comprising components which are incompatible with each other, i.e. components which react with each other at ambient temperature, and to a method for preserving and packaging said cosmetic compositions.

Several disadvantages have been observed with respect to the marketing of commercially available cosmetic compositions of the aforementioned type. For instance, it is known that in hair dye compositions containing direct dyes, such as indamines, indoanilines, indophenols and quinone imines, it is quite difficult to keep these dyes in aqueous solution and therefore it has generally been necessary to market them in the form of powders which are then put into solution at the time of use, or even, in the case of quinone imines, to prepare them at the time of application by mixing two solutions, one of which is an oxidizing agent. It has also been observed with respect to hair dye compositions containing (a) an oxidation dye, optionally including conventional couplers and (b) an oxidizing agent, the user must admix the various components immediately before application of the resulting dye composition to the hair. This arrangement also has a certain number of drawbacks because the user is not able most of the time to make a perfectly dosed mixture. To overcome these drawbacks it has been proposed to package these hair dye compositions in the form of microcapsules, but achieving such packaging often runs into major difficulties, when in particular it involves microencapsulating oxidizing agents such as hydrogen peroxide or volatile products such as ammonia. Further, in the case of hair dye compositions containing oxidation dyes, the composition before actually being applied to the hair is prepared, i.e. the components are admixed at ambient temperature, i.e., around 20°–25° C., which results in an extremely rapid initiation of the reaction of the components. Such a reaction rapidly degrades as far as the desired end product is concerned, because of the formation of secondary products. Therefore, it is necessary to admix these components very rapidly and, in any case, at the time of application of the hair dye composition to the hair it is not always possible to keep the reaction from already having produced a rather large amount of secondary products, thus making very difficult the attainment of reproducible shades.

It has also been recognized that it is quite difficult to store or keep conventional hair bleaching compositions at ambient temperature. For instance, it has been observed that on storage a slow decomposition of the persalts contained in these compositions occurs thereby reducing the activity of these hair bleaching compositions.

Prior efforts to resolve the problem of packaging and preserving these cosmetic compositions which contain two or more incompatible components, i.e., components which react together have been directed to the provision of specially adapted containers that have separate compartments for the various incompatible components. However, such containers are considerably more costly than regular or one-compartment packaging containers and for this reason it is often preferred to provide to the user of these cosmetic compositions the varius components packaged separately and let the user prepare the final composition at the time of use. This arrangement, however, entails a certain imprecision in the percentages or amounts of each component of the composition actually used, which leads to some difficulties, for instance, when the cosmetic composition is a hair dye, and when it is desired to reproduce exactly a given color or shade.

However, the present invention overcomes these disadvantages and actually makes it possible to preserve for a very long time completely prepared cosmetic compositions containing one or more components which, in solution, are unstable or react together at ambient temperature.

Accordingly one object of the present invention is to provide in a completely prepared cosmetic composition for treatment of hair or skin, which composition, containing as it does one or more components, is stable and which does not experience under storage conditions any appreciable reaction of any of the components thereof.

Another object of the present invention is to provide a cosmetic composition comprising one or more components which are incompatible or relatively unstable in solution at ambient temperature and wherein the initiation of the action or reaction of any of these components is essentially retarded or delayed until the time of use.

Another object of the present invention is to package in a one compartment container, two or more phases of a cosmetic composition for the hair or skin, each phase containing a component incompatible with a component present in one or more of the remaining phases.

The present invention also makes it possible, in the case of capillary hair dye compositions containing a component with a disagreeable odor, such as ammonia, to obtain a composition whose odor is considerably reduced or suppressed relative to one conventionally employed containing the same malodorous component.

Another object of the present invention is to package and preserve in an aerosol container a cosmetic composition which up until now has usually been prepared immediately before use because of its instability.

The present invention also makes it possible to package and preserve capillary compositions containing components which are capable of reacting together exothermically, thereby making it possible to apply to the hair a product at a temperature between 25° C. and 40° C. without creating a cold sensation on the scalp.

Finally, the invention also has the purpose of providing a cosmetic composition whose properties are as good as when it is prepared in the conventional way, i.e. immediately before use at ambient temperature, but which cosmetic composition has the advantage of being available to the user in a form practically ready for use, i.e. requiring no tedious or exacting measuring operations.

In accordance with the present invention, there is now provided a cosmetic composition, essentially ready for use, which is maintained at a temperature lower than its melting point or at the melting point of the component thereof having the lowest melting point when said composition comprises juxtaposed phases at least one of which contains a component incompatible with a component present in one or more of the remaining phases.

The present invention also relates to a method for stabilizing, preserving and packaging a cosmetic composition for the hair or skin, which composition at ambient temperature comprises a solution in a solvent selected from the group consisting of water and an aqueous lower alkanol solution of at least one cosmetic component which in said solution at ambient temperature is not stable on storage, the steps comprising admixing said component in said solvent to provide a solution thereof, immediately thereafter and before any appreciable activity or reactivity of said component or components occurs, subjecting the resulting solution to a temperature lower than the melting point of said solution to freeze the same in the form of a solid and maintaining the resulting frozen solid cosmetic at a temperature sufficiently low to prevent any appreciable thawing of the same until such time as it is desired to apply said cosmetic composition to the hair or skin.

In another embodiment of the present invention said cosmetic composition can be prepared by admixing one of said components with said solvent to provide a first admixture, subjecting the resulting first admixture to a temperature lower than the melting point of said first admixture thereby freezing said first admixure, admixing another of said components with said solvent to provide another admixture, introducing said another admixture in juxtaposed relationship to said frozen first admixture, subjecting said another admixture to a temperature lower than the melting point of said another admixture thereby freezing said second admixture, and maintaining said juxtaposed admixtures at a temperature sufficiently low to prevent thawing of the same until such time as it is desired to apply said cosmetic composition to the hair or skin.

Because of the very slight temperature rise of the cosmetic composition of this invention immediately after thawing, the said composition undergoes substantially less degradation than a conventional cosmetic composition which is prepared at the time of use at ambient temperature. Thus, the hair dye compositions or bleaching dye compositions of this invention provide results clearly superior to those usually achieved.

When the composition to be used comprises one or more components unstable in solution at ambient temperature, which is generally the case of direct dyes, such as indamines, indoanilines, indophenols or quinone imines, the composition is frozen immediately after its preparation by mixing of the various ingredients. Further, these frozen compositions can contain other components ordinarily employed in similar cosmetic preparations such as thickeners, swelling agents, perfumes, penetrating agents and the like. The cosmetic composition of this invention can also contain other dyes presenting no particular preservation difficulties such as azo dyes, anthraquinone dyes, nitro dyes of the benzene series, oxazine dyes and metal-bearing complex dyes.

The cosmetic composition of this invention can be in aqueous or dilute aqueous alcohol solution. They can also constitute capillary setting lotions, in which case, they comprise a dilute aqueous alcohol solution containing a cosmetic resin.

The frozen cosmetic composition of the present invention can also contain components which are able to react together exothermically, so as to obtain, after thawing, a composition whose temperature is between about 25° C. and 40° C.

The cosmetic composition of this invention can be frozen so as to obtain a relatively large size solid mass which can then be divided into several portions before being packaged or it can also be packaged in block form containing the amount required for one application and can be distributed in conventional containers such as plastic bags or any other similar container. The frozen cosmetic composition can be kept at a sufficiently low temperature to prevent premature thawing, for example, in the freezer compartment of a home refrigerator or in a conventional deep-freeze unit. Immediately before use, the user can easily heat a frozen block of the cosmetic composition either by letting it stand at ambient temperature for several minutes, or by mixing it with a brush or any other similar instrument, possibly adding a little water at ambient temperature, or by exposing it for several seconds to the action of a microwave oven.

The cosmetic composition of this invention can also be frozen directly in a conventional, single compartment container in amounts corresponding exactly to that required for a single application.

The container can then be kept in a home refrigerator or freezer as above and heated at the time of use by simply letting it stand for some minutes at ambient temperature, by passage in a microwave oven, by placing the container under the hot water faucet or any other similar means.

The cosmetic composition of this invention can also be introduced into an aerosol container together with a conventional aerosol propellant. Optionally, the aerosol container can be provided with a removable valve and means for releasably confining a recharge of the aerosol propellant. In either case, the assembly is frozen by subjecting the aerosol container to a source of cold. The container can then be kept in the freezer compartment of a home refrigerator or a deep-freeze unit. At the time of use, the aerosol container or said recharge is heated as above and a capillary composition is obtained ready for use in the form of an aerosol.

In all cases the cosmetic composition of this invention is frozen by subjecting it to a temperature below its freezing point, in general, around $-70°$ C., obtained by a mixture of solid carbon dioxide and ethanol, by a liquified gas such as nitrogen, or by any other source of cold conventionally employed. The said frozen cosmetic composition is then stored at a temperature between about $-10°$ and $-40°$ C. to prevent premature thawing of the same.

When thawed, the cosmetic composition of the present invention can be in the form of simple aqueous or dilute alkanol solution. It can also be in the form of a cream, gel or oil.

In the case of a cosmetic composition containing one or more components incompatible with one another, such as an oxidation dye which heretofore had to be mixed at the time of use with an oxidation agent, it is possible to proceed in the usual way by freezing at a temperature below the freezing point the composition obtained after mixing of the various components to avoid the development of a degradation reaction, which would otherwise occur at ambient temperature. However, it is advisable to avoid two eutectics obtained by mixing water and hydrogen peroxide so as to obtain a composition that can be stored in a home refrigerator.

It is also possible in this case to freeze first one of the components directly in the packaging container and then to add the second component in liquid state on the frozen layer formed by the first component. Any degradation reaction that might occur at the interface between the two layers is practically negligible, because of the very low temperature of the frozen layer. A second freezing makes it possible to obtain a cosmetic composition with two incompatible components in the form of two frozen layers in the same packaging container. Of course, it is also possible to obtain in the same way frozen layers of several components incompatible in pairs. This latter method makes it possible, in the situation where the composition presents a particularly low eutectic, not to go down to the temperature of this eutectic, but, rather, to freeze the same at the freezing point of the various components taken separately.

When it is desired to use the frozen cosmetic composition of this invention, the same is thawed sufficiently to attain a consistency suitable for application to the hair or skin, and generally the temperature of the cosmetic composition at the time of application can be rather low, i.e. about +5° C., which temperature considerably slows down the reaction between the various components or inhibits or substantially prevents any degradation reaction.

Thus, in all cases remarkable results are obtained in treating hair with compositions preserved and packaged according to the process of the present invention, and the present process and the fact that the compositions can be dosed very exactly before freezing, provides for the attainment of perfectly reproducible shades in the case of dyeing or bleaching capillary compositions.

As stated above, the present invention is particularly useful in the preparation of oxidation-type hair dye compositions. Illustrative of such compositions are those described, for instance, in U.S. Pat. Nos. 3,591,323; 3,563,684; 3,649,160; 3,658,455 and 3,674,414 incorporated herein by reference. Generally, in these compositions the oxidation base is present in amounts such that the mole ratio of base to coupler is 1:1 to 1:3 with the oxidizing agent such as hydrogen peroxide being present in amounts of about 4 to 12 percent by weight of the total composition.

Representative hair bleaching or bleaching-dyeing compositions usefully employed in the present invention are those set forth in U.S. Pat. No. 3,578,387, also incorporated herein by reference.

As hair restructuring compositions, those disclosed in U.S. Pat. Nos. 3,642,429; 3,661,161; 3,672,375 and 3,674,038 which are also incorporated herein by reference, can be employed in the practice of the present invention.

Cosmetic resins usefully employed to provide hair setting lotion compositions include, for instance, polyvinyl pyrrolidone having a molecular weight of 40,000-400,000, copolymer of crotonic acid and vinyl acetate, said copolymer having a molecular weight ranging from about 10,000 to 70,000, copolymer of vinyl pyrrolidone and vinyl acetate wherein the ratio of PVP to VA ranges between 50-70:50-30, said copolymer having a molecular weight ranging from about 30,000 to 200,000 and maleic anhydride-butylvinyl ether copolymer, a 1% solution of which in methylethyl ketone has a viscosity of 0.1-3.5 cps at 25° C. Generally, these resins are used in amounts of 1-3% by weight of the hair-setting lotion composition. Further, in these lotions the dye can be present in amounts of about 0.002-1 percent by weight of the total composition. And as stated, the solvent for these hair setting lotions is an aqueous alcohol solution, the alcohol being a lower alkanol including ethanol and isopropanol in amounts of 20 to 70 percent by weight of the hair-setting lotion composition.

The solvent for the cosmetic composition of the present invention is water or an aqueous alkanol solution, said alkanol being ethanol or isopropanol present in amounts of about 20-70 percent by weight of the total composition.

When a sprayable aerosol composition is provided a conventional aerosol propellant such as dichlorodifluoromethane, trichloromonofluoromethane and their mixtures can be used. Obviously other conventional aerosol propellants can also be employed.

The pH of the cosmetic compositions of the present invention can vary between about 2.5 to 12 depending upon, for instance, their ultimate use and purpose. The desired pH can be regulated by the use of alkalizing agents such as ammonia, mono-, di- or triethanolamine, and of acidifying agents such as phosphoric acid, acetic acid or lactic acid.

The present invention also makes it possible to prepare compositions for the care of the skin containing natural extracts of vegetal or animal origin, and which could not be stored in the ordinary conditions of temperature and packaging. These compositions can be in the form of aqueous or aqueous-alcoholic solutions and contain particularly plankton, fruit or vegetable extracts, serums, amniotic liquids, biologic extracts as polypeptide testicular or mammary extracts, polypeptide extracts of skin cells or of embryonic liver cells, enzymes ascytochrome C, pappaine, chymotrypsine, hyaluromidase, etc..

The following examples are intended to illustrate the present invention. Unless otherwise specified, all parts and percentages are by weight and all temperatures are expressed in degrees centigrade.

EXAMPLE 1

The following hair dye composition is prepared in gel form by mixing 30 g of part $A_1$ and 30 g of part $B_1$ defined below.

Part $A_1$

Nonylphenol oxyethylenated with 9 moles of ethylene oxide (sold under the name "Remcopal 349" by the Gerland Company): 20 g
Nonylphenol oxyethylenated with 4 moles of ethylene oxide (sold under the name "Remcopal 334" by the Gerland Company): 25 g
Dimethylbenzylammonium chloride: 1 g
Butylglycol: 10 g
Propyleneglycol: 10 g
Trilon B (sodium ethylene diamino tetraacetate): 3 g
Sodium bisulfite: 1 g
Ammonia at 22° Bé: 12 cc
Paratoluylenediamine: 1.5 g
Metaaminophenol: 0.2 g
Paraaminophenol: 0.1 g
Resorcin: 0.4 g
Metadiaminoanisole sulfate: 0.25 g
Hydroquinone: 0.15 g
Water, q.s.p.: 100 g

Part $B_1$ 200 volume hydrogen peroxide: 10 cc
Phenacetin: 0.05 g
Phosphoric acid, q.s.p. pH 3

Water, q.s.p.: 100 g

The resulting gel is immediately frozen at −70° C. by using a mixture of solid carbon dioxide and ethyl alcohol. The resulting frozen cosmetic composition, in solid form, is stored at −40° C. in a freezer compartment of a home refrigerator. At the time of use, the above frozen cosmetic composition is heated by mixing the same with a brush at ambient temperature. When the temperature of the composition reaches about 5° C. a gel is obtained which, when applied to black hair containing 20% white hair, imparts thereto in 30 minutes a very uniform brown shade which is identical with that obtained by the usual processes of mixing the same components at ambient temperature at the time of use.

EXAMPLE 2

The following hair dye composition is prepared in gel form by mixing 30 g of part $A_2$ and 30 g of $B_2$ defined below.

Part $A_2$

Nonylphenol oxyethylenated with 9 moles of ethylene oxide (sold under the name "Remcopal 349" by the Gerland Company): 10 g
Nonylphenol oxyethylenated with 4 moles of ethylene oxide (sold under the name "Remcopal 334" by the Gerland Company): 15 g
Oleic acid: 15 g
Ethyl alcohol, 96° titer: 10 g
Propyleneglycol: 15 g
Trilon B (sodium ethylene diamino tetraacetate): 3 g
Sodium bisulfite: 1 g
Ammonia at 22° Bé: 15 cc
Paratoluylenediamine: 1 g
Metaaminophenol: 0.1 g
Paraminophenol: 0.06 g
Resorcin: 0.3 g
Hydroquinone: 0.5 g
Water, q.s.p.: 100 g

Part $B_2$ 200 volume hydrogen peroxide: 10 cc
8-hydroxyquinolein: 0.01 g
Anhydrous sodium pyrophosphate: 0.03 g
Trilon B (sodium ethylene diamino tetraacetate): 0.02 g
Phosphoric acid, q.s.p. pH 3
Water, q.s.p.: 100 g The resulting gel is immediately frozen at −70° C. by using a mixture of solid carbon dioxide and ethyl alcohol. The resulting frozen cosmetic composition, in solid form, is stored at −40° C. in a freezer. At the time of use, the above frozen cosmetic composition is heated by letting the same stand for 10 minutes at ambient temperature. When the temperature of the composition reaches about 5° C., a gel is obtained, which, when applied to brown hair, imparts thereto in 40 minutes a very pretty chestnut brown shade, completely identical with that obtained by conventional procedures.

EXAMPLE 3

The following hair dye composition is obtained in gel form by mixing 30 g of Part $A_3$ and 30 g of Part $B_3$ defined below.

Part $A_3$

Nonylphenol oxyethylenated with 9 moles of ethylene oxide (sold under the name "Remcopal 349" by the Gerland Company): 12 g
Nonylphenol oxyethylenated with 4 moles of ethylene oxide (sold under the name "Remcopal 334" by the Gerland Company): 15 g
Oleic acid: 3 g
Trimethylcetylammonium bromide: 3 g
Copra diethanolamide: 7 g
Ethyl alcohol, 96° titer: 8 g
Propyleneglycol: 2 g
Butylglycol: 5 g
Sodium bisulfite: 1 g
Ammonia at 22° Bé: 12 cc
Paratoluylenediamine: 0.3 g
Metaaminophenol: 0.05 g
Paraaminophenol: 0.1 g
Resorcin: 0.2 g
Hydroquinone: 0.15 g
Water, q.s.p.: 100 g

Part $B_3$ 200 volume hydrogen peroxide: 20 cc
Water, q.s.p.: 100 cc

The resulting gel is immediately frozen at −70° C. by using a mixture of solid carbon dioxide and ethyl alcohol. The resulting frozen cosmetic composition, in solid form, is stored at −40° C. in a freezer. At the time of use, the above frozen cosmetic composition is heated by mixing the same with a brush at ambient temperature. When the temperature of the composition reaches about 5° C., a gel is obtained which, when applied to dark chestnut brown hair, imparts thereto, after a 40 minute contact period, a very pretty very luminous blond shade that is particularly aesthetic and completely identical with that obtained using a conventionally prepared dye having the same components and composition.

EXAMPLE 4

The following hair dye composition is prepared in the form of a cream by mixing 25 g of part $A_4$ and 25 g of part $B_4$ defined below.

Part $A_4$

Cetylstearyl alcohol: 25 g
Sodium cetylstearyl sulfate: 2 g
20% ammonia: 12 cc
Trilon B (sodium ethylene diamino tetraacetate): 3 g
Sodium bisulfite: 1 g
Paratoluylenediamine: 1 g
Metaaminophenol: 0.1 g
Paraaminophenol: 0.05 g
Resorcin: 0.3 g
Hydroquinone: 0.5 g
Water, q.s.p.: 100 g

Part $B_4$

Identical with Part $B_1$ of Example 1.

The resulting cream is introduced into a single compartment conventional packaging container which is immediately placed in a chamber at −70° C. by using a mixture of solid carbon dioxide and ethyl alcohol. The resulting frozen cosmetic composition, in solid form, is then stored at −40° C. in a freezer. At the time of use, the above frozen cosmetic composition is heated by mixing the same with a brush at ambient temperature. When the temperature of the composition reaches about 5° C., a cream is obtained, which when applied directly to brown hair, imparts thereto a very regular chestnut brown shade which is identical to that obtained by making the above mixture from the same components just before application at ambient temperature.

EXAMPLE 5

The following hair bleaching composition is prepared in cream form by mixing 20 g of powder $A_5$ and 40 g of solution $B_5$ defined below.

POWDER $A_5$

Sodium persulfate: 70 g
Ammonium chloride: 10 g
Sodium metasilicate: 10 g
Trilon B (sodium ethylene diamino tetraacetate): 1 g
Silica: 9 g

SOLUTION $B_5$

Identical with solution $B_2$ of Example 2.

The resulting cream is immediately frozen at $-70°$ C. by using a mixture of solid carbon dioxide and ethyl alcohol. The resulting frozen cosmetic composition, in solid form, is then stored at $-40°$ C. in a freezer. At the time of use, the above frozen cosmetic composition is heated by placing the same in a microwave oven for 20 seconds. When it comes from the oven the temperature of the composition is about 5° C. and a bleaching cream is obtained which when applied to chestnut brown hair, imparts thereto a light blond shade. The results are identical with those obtained by making the above mixture from the same components at the time of use at ambient temperature.

EXAMPLE 6

The following hair bleaching composition is prepared in oil form by mixing 30 g of solution $A_6$ and 30 g of solution $B_6$ defined below.

Solution $A_6$

Nonylphenol oxyethylenated with 4 moles of ethylene oxide (sold under the name of "Remcopal 334" by the Gerland Company): 30 g
Nonylphenol oxyethylenated with 9 moles of ethylene oxide (sold under the name "Remcopal 349" by the Gerland Company): 25 g
Butylglycol: 15 g
Propyleneglycol: 5 g
20% ammonia: 20 cc
Trilon B (sodium ethylene diamino tetraacetate): 0.1 g
Water, q.s.p.: 100 g

Solution $B_6$ 200 volume hydrogen peroxide: 15 cc
8-hydroxyquinolein: 0.01 g
Anhydrous sodium pyrophosphate: 0.03 g
Trilon B (sodium ethylene diamino tetraacetate): 0.02 g
Phosphoric acid, q.s.p. pH 3
Water, q.s.p.: 100 g The resulting oil is immediately frozen at $-70°$ C. by using a mixture of solid carbon dioxide and ethyl alcohol. The resulting frozen cosmetic composition, in solid form, is then stored at $-40°$ C. in a freezer. At the time of use, the above frozen cosmetic composition is heated by mixing the same with a brush at ambient temperature. When the temperature of the composition reaches about 5° C., an oil is obtained which when applied to chestnut brown hair imparts thereto a blond coloration which is the same as that obtained by making the oil from the same components just before use at ambient temperature. Further, because of the low temperature of the oil of this invention at the time of application the ammonia odor is extremely reduced.

EXAMPLE 7

There are frozen at $-70°$ C. with a mixture of solid carbon dioxide and ethyl alcohol, 25 cc of part $A_7$ defined below after it has been poured into a single compartment conventional packaging container.

Part $A_7$

Hydroxethylcellulose (sold under the name "Natrosol 250 L" by the Hercules Powder Company): 1 g
4-hydroxy 2',4'-diamino 5'-methoxy diphenylamine dichloride monohydrate: 3 g
20 volume hydrogen peroxide: 10 cc
Phosphoric acid, q.s.p. pH 3
Water, q.s.p.: 100 cc Then there are poured onto the frozen layer formed by part $A_7$, 10 cc of part $B_7$ defined below.

Part $B_7$

Sodium bisulfite at 33°Bé: 100 g

The resulting frozen cosmetic composition, thus packaged, is then stored at $-40°$ C. in a home freezer. At the time of use, heating is performed by letting the container stand at ambient temperature for 2 minutes.

Because of the oxidation-reduction reaction, thawing of the cosmetic composition is considerably accelerated and a product having a temperature between 25° C. and 40° C. is very rapidly obtained. When applied for 10 minutes to hair dyed copper chestnut brown, it imparts to the hair, after rinsing, a pretty dark auburn brown shade.

EXAMPLE 8

There are frozen at $-70°$ C. with a mixture of solid carbon dioxide and ethyl alcohol, 25 cc of part $A_8$ defined below after it has been poured into a single compartment conventional packaging container.

Part $A_8$ hydroxyethylcellulose (sold under the name of "Natrosol 250 L" by the Hercules Powder Company): 0.5 g
200 volume hydrogen peroxide: 15 cc
N-[(4'-hydroxy) phenyl]3-amino 6-methyl benzoquinoneimine: 2 g
Phosphoric acid, q.s.p. pH 3
Water, q.s.p.: 100 cc 10 cc of part $B_8$, defined below, are then poured on the frozen layer formed by part $A_8$.

Part $B_8$

Sodium bisulfite at 33°Bé: 98 g
Ammonia at 22°Bé: 2 g

The resulting frozen cosmetic composition, thus packaged, is then stored at $-40°$ C. in the freezer of a domestic refrigerator. At the time of use, the cosmetic composition is heated by leaving the container at ambient temperature for 2 minutes.

Because of the oxidation-reduction reaction thawing of the cosmetic composition is considerably accelerated and a product having a final temperature between 25° C. and 40° C. is very rapidly obtained. When applied for 10 minutes to naturally blond hair, it imparts thereto, after rinsing, a pretty dark auburn brown shade.

EXAMPLE 9

25 cc of part $A_9$ defined below, after being poured into a packaging container, is frozen at $-70°$ C. with a mixture of solid carbon dioxide and ethyl alcohol.

Part $A_9$

Hydroxyethylcellulose (sold under the name "Natrosol 250 L" by the Hercules Powder Company): 1.5 g
200 volume hydrogen peroxide: 15 cc
Dye Blue Cibalane BRL of the CIBA Company (CI: acide blue 171): 0.3 g pl Phosphoric acid, q.s.p. pH 3
Water, q.s.p.: 100 cc Then 10 cc of part $B_9$ defined below are poured on the frozen layer formed by part $A_9$.

Part $B_9$

Sodium bisulfite at 33°Bé: 100 g

The resulting frozen cosmetic composition, thus packaged, is then stored at $-40°$ C. in a home freezer. At the time of use, the cosmetic composition is heated by letting the container stand at ambient temperature for 1 minute.

Because of the rapid oxidation-reduction reaction, thawing is considerably accelerated and a product having a final temperature of 30° to 40° C. is obtained. When applied for 10 minutes to chestnut brown hair, this dye composition imparts thereto, after rinsing, a slight brightening and the hair has a pretty ash glint.

EXAMPLE 10

The following hair restructuring composition $S_{10}$ is prepared as follows.

Composition $S_{10}$

Monomethyloldicyandiamide: 10 g
Cetylpyridinium bromide: 0.1 g
Phosphoric acid, q.s.p. pH 2.5
Water, q.s.p.: 100 g The above components are admixed and the resulting solution is introduced into a packaging container which is immediately plunged into liquid nitrogen. The resulting frozen cosmetic composition is then stored at $-40°$ C. in a home freezer. At the time of use, the frozen cosmetic composition is heated by placing the same for 30 seconds in a microwave oven, which causes thawing of the solution.

This solution is then applied to hair that has undergone numerous bleachings. After drying under a drier for 30 minutes at 45° C., the hair is then permanently waved with a reducing solution containing ammonium thioglycolate in the usual way.

Then a standard type setting is performed and it is found that the hair thus treated presents a good liveliness, brillance and cosmetic qualities clearly improved in comparison with hair given a usual permanent wave treatment.

EXAMPLE 11

The following hair restructuring composition $S_{11}$ defined below is prepared.

Solution $S_{11}$

Methyl ether monomethyloldicyandiamide: 6 g
Cetylpyridinium bromide: 0.1 g
Vinyl acetate/polyvinylpyrrolidone copolymer (MW 40000 à 400.000): 0.5 g
Acetic acid, q.s.p. pH 3
Water, q.s.p.: 100 cc The above components are admixed and the resulting solution is frozen as in Example 10. After thawing, similar to that of Example 10, this lotion is applied to hair previously having undergone several permanents. After drying, hardened brilliant hair is obtained and the hair-do presents an appearance quite superior to that of a hair given a conventional permanent.

EXAMPLE 12

There are introduced into an aerosol container 60 g of the gel obtained in Example 1 by mixing part $A_1$ and part $B_1$ in the proportions specified in Example 1 and 6 g of a propellant comprising a 70/30 mixture of dichlorotetrafluoroethane (Freon 114) and dichlorodifluoromethane (Freon 12). The aerosol container thus filled is plunged into liquid nitrogen which causes freezing of the composition contained therein.

The aerosol container is then stored at $-40°$ C. in a home freezer. At the time of use, the container is allowed to stand at ambient temperature for 10 minutes to thaw the contents thereof.

After thawing, a dye is obtained ready for use, packaged under pressure in aerosol form and which is dispensed from the container in the form of an aerated foam. Storage of such an aerosol composition was not possible before, because its dyeing power very rapidly decreased once the mixture was made.

However, when the hair dye composition of this invention, as described above, is applied to black hair containing 20% white hair, the results obtained are identical with those of Example 1.

EXAMPLE 13

There are introduced into a case constituting a recharge of an aerosol container with a removable valve, 60 g of the gel obtained in Example 2, by mixing part $A_2$ and part $B_2$ in the proportions specified in Example 2, and 10 g of Freon 114 as the propellant.

The case is then plunged into liquid nitrogen to freeze the dyeing composition contained therein. Under these conditions, the vapor tension of Freon 114 is less than the atmosphere. The recharge of the aerosol container is then stored at $-40°$ C. in a home freezer.

At the time of use, the contents of the case are introduced into an aerosol with a removable valve and there is obtained, after thawing, a dye ready for use which when applied to brown hair imparts thereto results identical with those of Example 2.

EXAMPLE 14

The following day cream is prepared:
Stearic acid: 2 g
Cosbiol: 20 g
Auto-emulsionnable glycerol monostearate: 2 g
Triethanolamine: 1.3 g Preserving agent: 0.3 g
Carbopol 941: 0.3 g
Crude thermal plankton: 20 cm³
Rose extract: 0.3 g
H₂O q.s.p.: 100 g The mixture is stirred until a complete homogeneity is obtained and then cooled while stirring until a temperature of about 10° C.-0° C. is reached. The stirring is stopped and the mixture is placed into dose-unit containers having a tubular or tronc-pyramidal form. After having obturated the containers the whole is frozen at −70° C. using a mixture of solid carbon dioxide and alcohol. The cream is then in a solid form which can be stored at a temperature of −15° C. to −25° C.

At the time of use, the cream is placed at the ambiant temperature while slowly stirring with a spatula until the temperature reaches about 0° C. to 5° C.

The day cream of the invention is then ready for using.

EXAMPLE 15

The following day cream is prepared:
Stearic acid: 2 g
Cosbiol: 20 g
Auto-emulsionnable glycerol monostearate: 2 g
Triethanolamine: 1.3 g
Preserving agent: 0.3 g
Carbopol 941: 0.3 g
Vegetal extracts: 20 g
Rose extract: 0.3 g
H₂O q.s.p.: 100 g
and it is processed as in example 14.

The vegetal extracts mentionned in the above composition are choozen among fruit or vegetable extracts used in cosmetics as extracts of ananas, strawberry, apricot, carrot, cucumber, etc.

EXAMPLE 16

The following regenerating night cream is prepared:
Stearic acid: 2 g
Cosbiol: 20 g
Autoemulsionnable glycerol monostearate: 2 g
Triethanolamine: 1.3 g
Preserving agent: 0.3 g
Carbopol 941: 0.3 g
Horse serum: 4 g
Perfume: 0.3 g
H₂O q.s.p.: 100 g
and it is processed as in example 14, but the storage temperature is −25° C. to −35° C.

EXAMPLE 17

The following regenerating night cream is prepared:
Stearic acid: 2 g
Cosbiol: 20 g
Auto-emulsionnable glycerol monostearate: 2 g
Triethanolamine: 1.3 g
Preserving agent: 0.3 g
Carbopol 941: 0.3 g
Amniotic liquid: 10 g
Perfume: 0.3 g
H₂O q.s.p.: 100 g
and it is processed as in example 14, but the storage temperature is −20° C. to −30° C.

EXAMPLE 18

The following treating cream is prepared:
Stearic acid: 2 g
Cosbiol: 20 g
Auto-emulsionnable glycerol monostearate: 2 g
Triethanolamine: 1.3 g
Preserving agent: 0.3 g
Carbopol 941: 0,3 g
Embryonnic lever extracts: 0.05 a 2 g
Perfume: 0.3 g
H₂O q.s.p.: 100 g
and it is processed as in example 14, but the storage temperature is about −40° C.

EXAMPLE 19

The following "mask-composition" is prepared:
Auto-emulsionnable wax: 8 g
Cetylic alcohol: 8 g
Paraffin: 6 g
Polypropyleneglycol: 4 g
Propyleneglycol: 8 g
Proteol SN: 12 g
Preserving agent: 0.3 g
Pappaine: 8 g
Perfume: 1 g
H₂O q.s.p.: 100 g
and it is processed as in example 14, but the storage temperature is about −40° C.

What is claimed is:
1. A solid frozen stabilized hair dye composition adapted to be thawed at a temperature of at least about +5° C. to a cream or gel comprising a solution of a solvent selected from the group consisting of water and an aqueous alcohol solution, said alcohol being present in an amount of about 20 to 70% by weight of the total composition an oxidation hair dye and an oxidation agent wherein said solid frozen stabilized hair dye composition is in the form of a single use solid portion packaged in a single compartment container comprising a first frozen layer comprising said oxidation hair dye and a second frozen layer comprising said oxidation agent, said first and second layers being juxtaposed in said container, whereby the temperature of said thawed composition when applied to the hair in an amount effective to dye said hair, rises only slightly, whereby said composition undergoes substantially less degradation than conventional dye composition prepared at the time of use at ambient temperature.

* * * * *